United States Patent
Guo et al.

(10) Patent No.: US 8,865,444 B1
(45) Date of Patent: Oct. 21, 2014

(54) β-MANNANASE HAVING IMPROVED ENZYMATIC ACTIVITY (71) Applicant: Dongguan APAC Biotechnology Co., Ltd., DongGuan (CN)

(72) Inventors: Rey-Ting Guo, Taipei (TW); Jian-Wen Huang, Taipei (TW); Ya-Shan Cheng, Taipei (TW); Tzu-Hui Wu, Taipei (TW); Hui-Lin Lai, Taipei (TW); Cheng-Yen Lin, Taipei (TW); Ting-Yung Huang, Taipei (TW)

(73) Assignee: Dongguan APAC Biotechnology Co., Ltd., DongGuan (CN)

( * ) Notice: Subject to any disclaimer, the term of this patent is extended or adjusted under 35 U.S.C. 154(b) by 0 days.

(21) Appl. No.: 14/019,263

(22) Filed: Sep. 5, 2013

(30) Foreign Application Priority Data

Apr. 17, 2013 (TW) .............................. 102113688 A (51) Int. Cl.
*C12N 9/24* (2006.01)

(52) U.S. Cl.
CPC ................................... *C12N 9/2491* (2013.01)
USPC ......................................................... 435/200

(58) Field of Classification Search
None
See application file for complete search history.

(56) References Cited

PUBLICATIONS

Cuong et al., "Cloning, expression in *Pichia pastoris*, and characterization of a thermostable GH5 mannan endo-1,4-beta-mannosidase from *Aspergillus niger* BK01", Microbial Cell Factories, 2009, 8:59. doi:10.1186/1475-2859-8-59.*

* cited by examiner

*Primary Examiner* — Suzanne M Noakes
(74) *Attorney, Agent, or Firm* — Kirton McConkie; Evan R. Witt (57) ABSTRACT

A β-mannanase having increased enzymaic activity is disclosed. The β-mannanase has a modified amino acid sequence of SEQ ID NO: 2, wherein the modification is a substitution of Tyrosine at position 216 with Tryptophan.

8 Claims, 4 Drawing Sheets

```
tccttcgcttccacttccggattgcagttcactattgacggtgagactggttacttcgctggaactaactcctactggatcggtttcttg
 S  F  A  S  T  S  G  L  Q  F  T  I  D  G  E  T  G  Y  F  A  G  T  N  S  Y  W  I  G  F  L actgacaacgctgacgttgacttggttatgggtcacttgaagtcctccggtttgaagatcttgagagttggggtttcaacgacgttact
 T  D  N  A  D  V  D  L  V  M  G  H  L  K  S  S  G  L  E  I  L  R  V  G  F  N  D  V  T tccaaccatcctccggtactgttggtatcaatgcaccaggacggaaagtccactatcaacactggtgctgacggattgcagagattg
 S  Q  P  S  S  G  T  V  W  Y  Q  L  H  Q  D  G  K  S  T  I  N  T  G  A  D  G  L  Q  R  L gactacgttgttcctccgctgagcagcacgacatcaagcttatcatcaacttcgttaactactggactgactacggtggtatgtccgct
 D  Y  V  V  S  A  E  Q  H  D  I  K  L  I  I  N  F  V  N  Y  W  T  D  Y  G  G  M  S  A tacgtttctgcttatggtggttctggtgagactgacttctacacttccgacactatgcagtccgcttaccagacttacatcaagactgtt
 Y  V  S  A  Y  G  G  S  G  E  T  D  F  Y  T  S  D  T  M  Q  S  A  Y  Q  T  Y  I  K  T  V gttgagagataatccaactcctccgctgttttcgcttgggaattggctaacgagccaagatgtccttcctgtgacacttccgtcttgtac
 V  E  R  Y  S  N  S  S  A  V  F  A  W  E  L  A  N  E  P  R  C  P  S  C  D  T  S  V  L  Y aactggatcgaaaagacttccaagttcatcaagggtttggacgctgacagaatggtctgtattggtgacgagggtttcggtttgaacatt
 N  W  I  E  K  T  S  K  F  I  K  G  L  D  A  D  R  M  V  C  I  G  D  E  G  F  G  L  N  I gactctgacggttcctacccataccaattctccgagggtttgaacttcactatgaacttggacatcgacactatcgacttcggtacattg
 D  S  D  G  S  Y  P  Y  Q  F  S  E  G  L  N  F  T  M  N  L  D  I  D  T  I  D  F  G  T  L cacttgtacccagactcttggggtacttctgatgattggggtaacggttggatcactgctcatggtgctgcttgtaaggctgctggtaag
 H  L  Y  P  D  S  W  G  T  S  D  D  W  G  N  G  W  I  T  A  R  G  A  A  C  K  A  A  G  K ccatgttgttggaagagtacggtgttacttccaaccactgttctgttgagggtgcttggcaaaagactgctttgtccactactggtgtt
 P  C  L  L  E  E  Y  G  V  T  S  N  H  C  S  V  E  G  A  W  Q  K  T  A  L  S  T  T  G  V ggtgctgacttgttctggcaatacggtgacgacttgtccactggtaagtctccagatgacggtaacactatctactacggtacttccgac
 G  A  D  L  F  W  Q  Y  G  D  D  L  S  T  G  K  S  P  D  D  G  N  T  I  Y  Y  G  T  S  D taccagtgtttggttactgaccacgttgctgctatcggttccgcttaa    -SEQ ID NO: 1
 Y  Q  C  L  V  T  D  H  V  A  A  I  G  S  A  *      -SEQ ID NO: 2
```

| Mutant | Primer sequence (SEQ ID NO: 7) |
|---|---|
| Y216W | 5'- CATTGACTCTGACGGTTCCTGGCCATACCAATTCTCCGAG -3' |

FIG. 3

```
tccttcgttccactcccggattgcagttcactattgacggtgagactggttacttcgctggaactaactcctactggatcggttcttg
 S  F  A  S  T  G  L  Q  F  T  I  D  G  E  T  G  Y  F  A  G  T  N  S  Y  W  I  G  F  L actgacaacgctgacgttgacttggttatgggtcacttgaagtctccggttgaagatcttgagagtttgggtttcaacgacgttact
 T  D  N  A  D  V  D  L  V  M  G  H  L  K  S  G  L  K  I  L  E  V  G  F  N  D  V  T tcccaaccatcctccggtactgtttggtatcaattgcaccaggacggaaagtccactatcaacactggtgctgacggattgcagagattg
 S  Q  P  S  S  G  T  V  W  Y  Q  L  H  Q  D  G  K  S  T  I  N  T  G  A  D  G  L  Q  R  L gactacgttgtttcctccgctgagcagcacgacatcaagcttatcatcaacttcgttaactactggactgactacggtggtatgtccgct
 D  Y  V  V  S  A  E  Q  H  D  I  K  L  I  I  N  F  V  N  Y  W  T  D  Y  G  G  M  S  A tacgtttctgcttatggtggttctggtgagactgactccttcacacttccgacactatgcagtccgcttaccagacttacatcaagactgtt
 Y  V  S  A  Y  G  G  S  G  E  T  D  F  T  T  S  D  T  M  Q  S  A  Y  Q  T  Y  I  K  T  V gttgagcgatactccaactcctccgctgtttttcgcttgggaattggctaacgagccaagatgtcttcctgtgacacttccgtcttgtac
 V  E  R  Y  S  N  S  S  A  V  F  R  L  G  N  W  L  T  S  Q  D  V  F  L  C  D  T  S  V  L  Y aactggatcgaaagattccaagtcatcaagggtttggacgctgacagaatggtctgtattggtgacgagggtttcggtttgaacatt
 N  W  I  E  K  T  S  F  I  K  G  L  D  A  D  R  N  V  C  I  G  D  E  G  F  G  L  N  I gactctgacggttccWggccataccaattctccgagggtttgaacttcactatgaacttggacatcgacactatcgacttcggtacattg
 D  S  D  G  S [W] P  Y  Q  F  S  E  G  L  N  F  T  M  N  L  D  I  D  T  I  D  F  G  T  L cacttgtaccagagacttcttgggtacttctgatgattggggtaacggttggatcactgctcatggtgctgcttgtaaggctgctggtaag
 H  L  Y  P  S  W  G  T  S  D  D  W  G  N  G  W  I  T  A  H  G  A  A  C  K  A  A  G  K ccatgttttgttggaagagtacggtgttacttccaaccactgttctgttgagggtgcttggcaaaagactgctttgtccactactggtgtt
 P  C  L  L  E  E  Y  G  V  T  S  N  H  C  S  V  E  G  A  W  Q  K  T  A  L  S  T  T  G  V ggtgctgacttgttctggcaatacggtgacgacttgtccactggtaagtctccagatgacggtaacactatctactacggtacttccgac
 G  A  D  L  F  W  Q  Y  G  D  D  L  S  T  G  K  S  P  D  D  G  N  T  I  Y  Y  G  T  S  D taccagtgtttggttactgaccacgttgctgctatcggttccgcttaa              -SEQ ID NO: 3
 Y  Q  C  L  V  T  D  H  V  A  A  I  G  S  A  *               -SEQ ID NO: 4
```

FIG. 4

| Enzyme | Specific Activity (unit/mg) |
|---|---|
| Wild-type | 646 |
| Y216W | 784 |

FIG. 5

| Enzyme | $k_{cat}$ (s$^{-1}$) | $K_m$ (mg/mL) | $k_{cat}/K_m$ (ml s$^{-1}$ mg$^{-1}$) |
|---|---|---|---|
| Wild-type | 1803 | 0.79 | 2279 |
| Y216W | 2217 | 1.01 | 2190 |

FIG. 6

SEQUENCE LISTING

<160> NUMBER OF SEQ ID NOS: 7

<210> SEQ ID NO 1
<211> LENGTH: 1038
<212> TYPE: DNA
<213> ORGANISM: Aspergillus niger BK01

<400> SEQUENCE: 1

```
tccttcgctt ccacttccgg attgcagttc actattgacg gtgagactgg ttacttcgct      60
ggaactaact cctactggat cggtttcttg actgacaacg ctgacgttga cttggttatg     120
ggtcacttga agtcctccgg tttgaagatc ttgagagttt ggggtttcaa cgacgttact     180
tcccaaccat cctccggtac tgtttggtat caattgcacc aggacggaaa gtccactatc     240
aacactggtg ctgacggatt gcagagattg gactacgttg tttcctccgc tgagcagcac     300
gacatcaagc ttatcatcaa cttcgttaac tactggactg actacggtgg tatgtccgct     360
tacgtttctg cttatggtgg ttctggtgag actgacttct acacttccga cactatgcag     420
tccgcttacc agacttacat caagactgtt gttgagagat actccaactc ctccgctgtt     480
ttcgcttggg aattggctaa cgagccaaga tgtccttcct gtgacacttc cgtcttgtac     540
aactggatcg aaaagacttc caagttcatc aagggtttgg acgctgacag aatggtctgt     600
attggtgaca agggtttcgg tttgaacatt gactctgacg ttcctaccc ataccaattc      660
tccgagggtt tgaacttcac tatgaacttg gacatcgaca ctatcgactt cggtacattg     720
cacttgtacc cagactcttg gggtacttct gatgattggg gtaacggttg gatcactgct     780
catggtgctg cttgtaaggc tgctggtaag ccatgttttg tggaagagta cggtgttact     840
tccaaccact gttctgttga gggtgcttgg caaaagactg cttttgtcca ctactggtgtt    900
ggtgctgact tgttctggca atacggtgac gacttgtcca ctggtaagtc tccagatgac     960
ggtaacacta tctactacgg tacttccgac taccagtgtt tggttactga ccacgttgct    1020
gctatcggtt ccgcttaa                                                   1038
```

<210> SEQ ID NO 2
<211> LENGTH: 345
<212> TYPE: PRT
<213> ORGANISM: Aspergillus niger BK01

<400> SEQUENCE: 2

```
Ser Phe Ala Ser Thr Ser Gly Leu Gln Phe Thr Ile Asp Gly Glu Thr
  1               5                  10                  15

Gly Tyr Phe Ala Gly Thr Asn Ser Tyr Trp Ile Gly Phe Leu Thr Asp
                 20                  25                  30

Asn Ala Asp Val Asp Leu Val Met Gly His Leu Lys Ser Ser Gly Leu
             35                  40                  45

Lys Ile Leu Arg Val Trp Gly Phe Asn Asp Val Thr Ser Gln Pro Ser
     50                  55                  60

Ser Gly Thr Val Trp Tyr Gln Leu His Gln Asp Gly Lys Ser Thr Ile
 65                  70                  75                  80

Asn Thr Gly Ala Asp Gly Leu Gln Arg Leu Asp Tyr Val Val Ser Ser
                 85                  90                  95

Ala Glu Gln His Asp Ile Lys Leu Ile Ile Asn Phe Val Asn Tyr Trp
            100                 105                 110

Thr Asp Tyr Gly Gly Met Ser Ala Tyr Val Ser Ala Tyr Gly Gly Ser
        115                 120                 125

Gly Glu Thr Asp Phe Tyr Thr Ser Asp Thr Met Gln Ser Ala Tyr Gln
```

```
                    130                 135                 140
Thr Tyr Ile Lys Thr Val Val Glu Arg Tyr Ser Asn Ser Ser Ala Val
145                 150                 155                 160

Phe Ala Trp Glu Leu Ala Asn Glu Pro Arg Cys Pro Ser Cys Asp Thr
                165                 170                 175

Ser Val Leu Tyr Asn Trp Ile Glu Lys Thr Ser Lys Phe Ile Lys Gly
            180                 185                 190

Leu Asp Ala Asp Arg Met Val Cys Ile Gly Asp Glu Gly Phe Gly Leu
        195                 200                 205

Asn Ile Asp Ser Asp Gly Ser Tyr Pro Tyr Gln Phe Ser Glu Gly Leu
210                 215                 220

Asn Phe Thr Met Asn Leu Asp Ile Asp Thr Ile Asp Phe Gly Thr Leu
225                 230                 235                 240

His Leu Tyr Pro Asp Ser Trp Gly Thr Ser Asp Asp Trp Gly Asn Gly
                245                 250                 255

Trp Ile Thr Ala His Gly Ala Ala Cys Lys Ala Ala Gly Lys Pro Cys
            260                 265                 270

Leu Leu Glu Glu Tyr Gly Val Thr Ser Asn His Cys Ser Val Glu Gly
        275                 280                 285

Ala Trp Gln Lys Thr Ala Leu Ser Thr Thr Gly Val Gly Ala Asp Leu
    290                 295                 300

Phe Trp Gln Tyr Gly Asp Asp Leu Ser Thr Gly Lys Ser Pro Asp Asp
305                 310                 315                 320

Gly Asn Thr Ile Tyr Tyr Gly Thr Ser Asp Tyr Gln Cys Leu Val Thr
                325                 330                 335

Asp His Val Ala Ala Ile Gly Ser Ala
            340                 345

<210> SEQ ID NO 3
<211> LENGTH: 1038
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 3
tccttcgctt ccacttccgg attgcagttc actattgacg gtgagactgg ttacttcgct      60
ggaactaact cctactggat cggtttcttg actgacaacg ctgacgttga cttggttatg     120
ggtcacttga gtcctccggt ttgaagatc ttgagagttt ggggtttcaa cgacgttact     180
tcccaaccat cctccggtac tgtttggtat caattgcacc aggacggaaa gtccactatc     240
aacactggtg ctgacggatt gcagagattg gactacgttg tttcctccgc tgagcagcac     300
gacatcaagc ttatcatcaa cttcgttaac tactggactg actacggtgg tatgtccgct     360 tacgttctg cttatggtgg ttctggtgag actgacttct acacttccga cactatgcag     420
tccgcttacc agacttacat caagactgtt gttgagagat actccaactc ctccgctgtt     480
ttcgcttggg aattggctaa cgagccaaga tgtccttcct gtgacacttc cgtcttgtac     540
aactggatcg aaaagacttc caagttcatc aagggtttgg acgctgacag aatggtctgt     600
attggtgacg agggtttcgg tttgaacatt gactctgacg gttcctggcc ataccaattc     660
tccgagggtt tgaacttcac tatgaacttg gacatcgaca ctatcgactt cggtacattg     720
cacttgtacc cagactcttg gggtacttct gatgattggg gtaacggttg gatcactgct     780
catggtgctg cttgtaaggc tgctggtaag ccatgtttgt tggaagagta cggtgttact     840
```

```
tccaaccact gttctgttga gggtgcttgg caaaagactg ctttgtccac tactggtgtt    900
ggtgctgact tgttctggca atacggtgac gacttgtcca ctggtaagtc tccagatgac    960
ggtaacacta tctactacgg tacttccgac taccagtgtt tggttactga ccacgttgct   1020
gctatcggtt ccgcttaa                                                  1038

<210> SEQ ID NO 4
<211> LENGTH: 345
<212> TYPE: PRT
<213> ORGANISM: Artificial Sequence
<220> FEATURE:
<223> OTHER INFORMATION: Sequence synthetically translated from SEQ ID
      NO: 3

<400> SEQUENCE: 4

Ser Phe Ala Ser Thr Ser Gly Leu Gln Phe Thr Ile Asp Gly Glu Thr
 1               5                  10                  15

Gly Tyr Phe Ala Gly Thr Asn Ser Tyr Trp Ile Gly Phe Leu Thr Asp
                20                  25                  30

Asn Ala Asp Val Asp Leu Val Met Gly His Leu Lys Ser Ser Gly Leu
            35                  40                  45

Lys Ile Leu Arg Val Trp Gly Phe Asn Asp Val Thr Ser Gln Pro Ser
        50                  55                  60

Ser Gly Thr Val Trp Tyr Gln Leu His Gln Asp Gly Lys Ser Thr Ile
65                  70                  75                  80

Asn Thr Gly Ala Asp Gly Leu Gln Arg Leu Asp Tyr Val Val Ser Ser
                85                  90                  95

Ala Glu Gln His Asp Ile Lys Leu Ile Ile Asn Phe Val Asn Tyr Trp
            100                 105                 110

Thr Asp Tyr Gly Gly Met Ser Ala Tyr Val Ser Ala Tyr Gly Gly Ser
        115                 120                 125

Gly Glu Thr Asp Phe Tyr Thr Ser Asp Thr Met Gln Ser Ala Tyr Gln
    130                 135                 140

Thr Tyr Ile Lys Thr Val Val Glu Arg Tyr Ser Asn Ser Ser Ala Val
145                 150                 155                 160

Phe Ala Trp Glu Leu Ala Asn Glu Pro Arg Cys Pro Ser Cys Asp Thr
                165                 170                 175

Ser Val Leu Tyr Asn Trp Ile Glu Lys Thr Ser Lys Phe Ile Lys Gly
            180                 185                 190

Leu Asp Ala Asp Arg Met Val Cys Ile Gly Asp Glu Gly Phe Gly Leu
        195                 200                 205

Asn Ile Asp Ser Asp Gly Ser Trp Pro Tyr Gln Phe Ser Glu Gly Leu
    210                 215                 220

Asn Phe Thr Met Asn Leu Asp Ile Asp Thr Ile Asp Phe Gly Thr Leu
225                 230                 235                 240

His Leu Tyr Pro Asp Ser Trp Gly Thr Ser Asp Asp Trp Gly Asn Gly
                245                 250                 255

Trp Ile Thr Ala His Gly Ala Ala Cys Lys Ala Ala Gly Lys Pro Cys
            260                 265                 270

Leu Leu Glu Glu Tyr Gly Val Thr Ser Asn His Cys Ser Val Glu Gly
        275                 280                 285

Ala Trp Gln Lys Thr Ala Leu Ser Thr Thr Gly Val Gly Ala Asp Leu
    290                 295                 300

Phe Trp Gln Tyr Gly Asp Asp Leu Ser Thr Gly Lys Ser Pro Asp Asp
305                 310                 315                 320
```

```
Gly Asn Thr Ile Tyr Tyr Gly Thr Ser Asp Tyr Gln Cys Leu Val Thr
                325                 330                 335

Asp His Val Ala Ala Ile Gly Ser Ala
            340                 345

<210> SEQ ID NO 5
<211> LENGTH: 52
<212> TYPE: DNA
<213> ORGANISM: Artificial Sequence
<220> FEATURE:
<223> OTHER INFORMATION: Synthetically generated primer

<400> SEQUENCE: 5
ggtattgagg gtcgcgcggc ggcggcggcg atgtccttcg cttccacttc cg            52

<210> SEQ ID NO 6
<211> LENGTH: 38
<212> TYPE: DNA
<213> ORGANISM: Artificial Sequence
<220> FEATURE:
<223> OTHER INFORMATION: Synthetically generated primer

<400> SEQUENCE: 6
agaggagagt tagagcctta agcggaaccg atagcagc                            38

<210> SEQ ID NO 7
<211> LENGTH: 40
<212> TYPE: DNA
<213> ORGANISM: Artificial Sequence
<220> FEATURE:
<223> OTHER INFORMATION: Synthetically generated primer

<400> SEQUENCE: 7
cattgactct gacggttcct ggccatacca attctccgag                          40
```

β-MANNANASE HAVING IMPROVED ENZYMATIC ACTIVITY

FIELD OF THE INVENTION

The present invention relates to a β-mannanase, and more particularly to a β-mannanase having improved enzymatic activity.

BACKGROUND OF THE INVENTION

β-1,4 Mannans are major components of hemicellulose in plant cell wall of softwood, plant seeds and beans. Four types of polysaccharides including linear mannan, galactomannan, glucomannan, galactoglucomannan that are linked via β-1,4-glycosidic bonds compose mannans. Mannan hydrolysis provides wide array of biotechnological applications, such as feed manufacture, pulp and paper industries, and hydrolyzing coffee extract to reduce viscosity. A set of enzymes are required for complete degradation of mannans, including endo-β-1,4-mannanase (β-mannanase, EC 3.2.1.78), exo-β-mannosidase (EC 3.2.1.25) to cleave the main chain, and β-glucosidase (EC 3.2.1.21), α-galactosidase (EC 3.2.1.22), and acetyl mannan esterase to remove side chain decoration. Among them, β-mannanase which catalyzes random hydrolysis of manno-glycosidic bonds in the main chain is the key enzyme. More recently, major products of β-mannanase, mannotriose and mannobiose (mannooligosaccharides, MOS), have been proved beneficial as animal nutrition additive due to its prebiotic properties.

β-Mannanases are derived from various organisms including bacteria, yeasts, and filamentous fungi. According to the amino acid sequence homology, β-mannanases are mostly classified to glycoside hydrolase (GH) families 5, 26 and 113. These families share the same $(\beta/\alpha)_8$ folding and catalytic machinery, that two glutamate residues at active site serve as general acid/base and nucleophile to catalyze the cleavage of glycosidic bonds via a retaining double displacement mechanisms. Since industrial process is usually carried out at high temperatures, stable enzyme usage under a broad range of temperature is highly desirable. Therefore, β-mannanase needs to be modified to meet the requirement for different industrial usages. There are two ways to achieve these goals, one way is to screen suitable genes in nature, and the second way is modifying current enzyme genes based on their 3-D structural information.

In the present invention, the crystal structure of β-mannanase is analyzed and the enzyme activity of β-mannanase is improved by site-directed mutagenesis of the gene.

SUMMARY OF THE INVENTION

An object of the present invention is to modify β-mannanase by means of structural analysis and site-directed mutagenesis to efficiently increase the enzyme activity, and improve its economic value of industrial application.

According to an aspect of the present invention, there is provided a β-mannanase having increased enzymaic activity. The β-mannanase has a modified amino acid sequence of SEQ ID NO: 2, wherein the modification is a substitution of Tyrosine at position 216 with Tryptophan.

In an embodiment, the amino acid sequence of SEQ ID NO: 2 is encoded by ManBK gene isolated from *Aspergillus niger* BK01, and the β-mannanase is an acidic and thermotolerant mannanase.

In an embodiment, the β-mannanase has a full length amino acid sequence of SEQ ID NO: 4.

According to another aspect of the present invention, there is provided a nucleic acid encoding the aforesaid β-mannanase, and a recombinant plasmid comprising the aforesaid nucleic acid.

According to an additional aspect of the present invention, there is provided an industrial use of the aforesaid β-mannanase, wherein the industrial use comprises uses in food industry, feed industry, and paper pulp industry.

The above objects and advantages of the present invention will become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

In the present invention, a gene of the β-mannanase ManBK was isolated from *Aspergillus niger* BK01, and ManBK is an acidic and thermotolerant β-mannanase. In order to improve the industrial application value of this enzyme, the protein structure of the apo-form ManBK was solved by X-ray crystallography, and the solved structure was superimposed with *Trichoderma reesei* mannanase (having 57% similarity in protein sequence compared with ManBK) in complex with mannobiose. Then, based on the structural information of the enzyme, the important amino acid residues in the active site were selected for site-directed mutagenesis to improve the enzymatic activity. The enzyme modification process of ManBK and the resulted mannanase protein are described in detail as follows.

Figure 1:
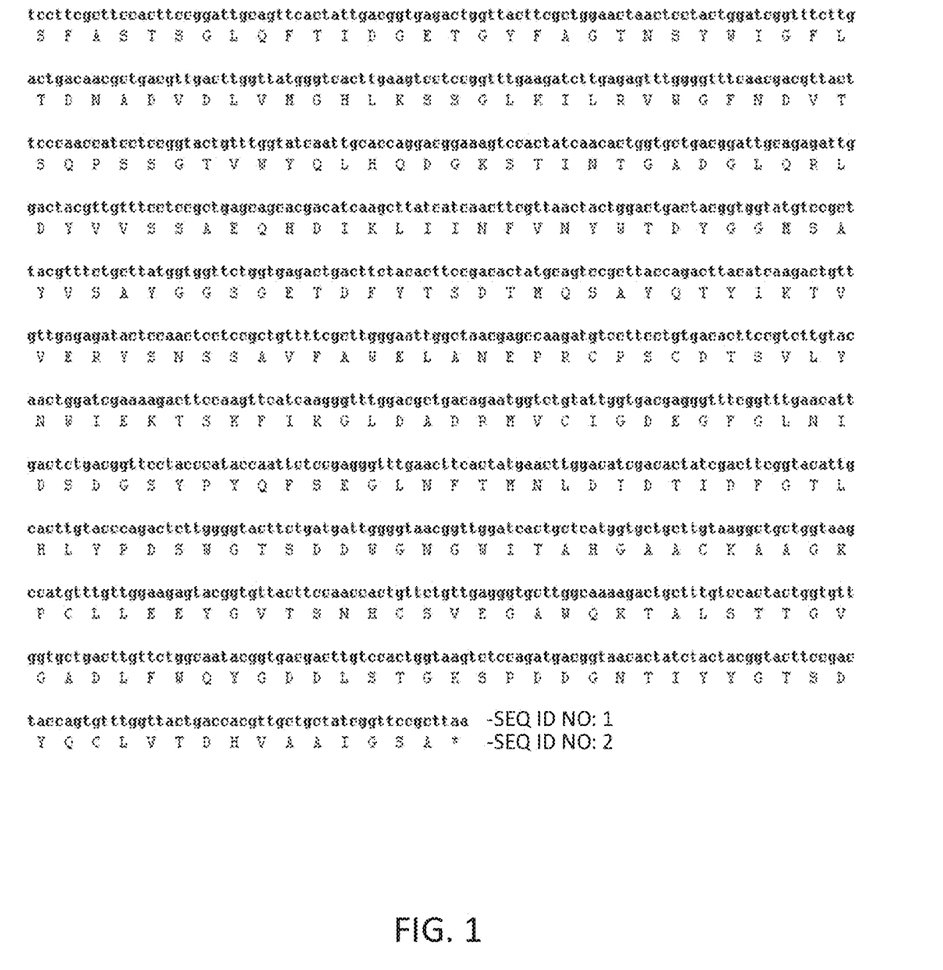
FIG. 1 shows the gene sequence and the amino acid sequence of the wild-type ManBK.

First, the ManBK gene was obtained from *Aspergillus niger* BK01 (GenBank accession no. FJ268574), and as shown in FIG. 1, the full length of sequence of the ManBK gene is 1038 base pairs (SEQ ID NO: 1), which encodes a protein of 345 amino acids (SEQ ID NO: 2). The ManBK gene was constructed into pPICZαA vector by using EcoRI and NotI sites. The primers for polymerase chain reaction were 5'-GGTATTGAGGGTCGCGCGGCGGCGGCG-GCGATG TCCTTCGCTTCCACTTCCG-3' (SEQ ID NO: 5, forward primer) and 5'-AGAGGAGAGTT AGAGCCT-TAAGCGGAACCGATAGCAGC-3' (SEQ ID NO: 6, reverse primer). The constructed plasmid was transformed into a competent cell as a wild-type expression vector.

To solve the protein structure of ManBK by X-ray crystallography, the protein crystal was obtained by using sitting drop vapor diffusion method at room temperature by Hampton screen kit. The protein crystal of ManBK in apo form was prepared by mixing 2 μl mannanase solution (10 mg/ml in 25 mM Tris-HCl, pH 7.5) with equal amounts of mixture solution and mother liquor, and equilibrating with 500 μl of the mother liquor at room temperature. The wild-type ManBK crystal was obtained by a condition composed of 0.1M Bis-Tris pH 5.5, 0.4M magnesium chloride, and 29% PEG3350. The molecular replacement method was used for phasing X-ray diffraction data, and the protein structure of ManBK was subsequently determined by crystallographic software.

Figure 2:
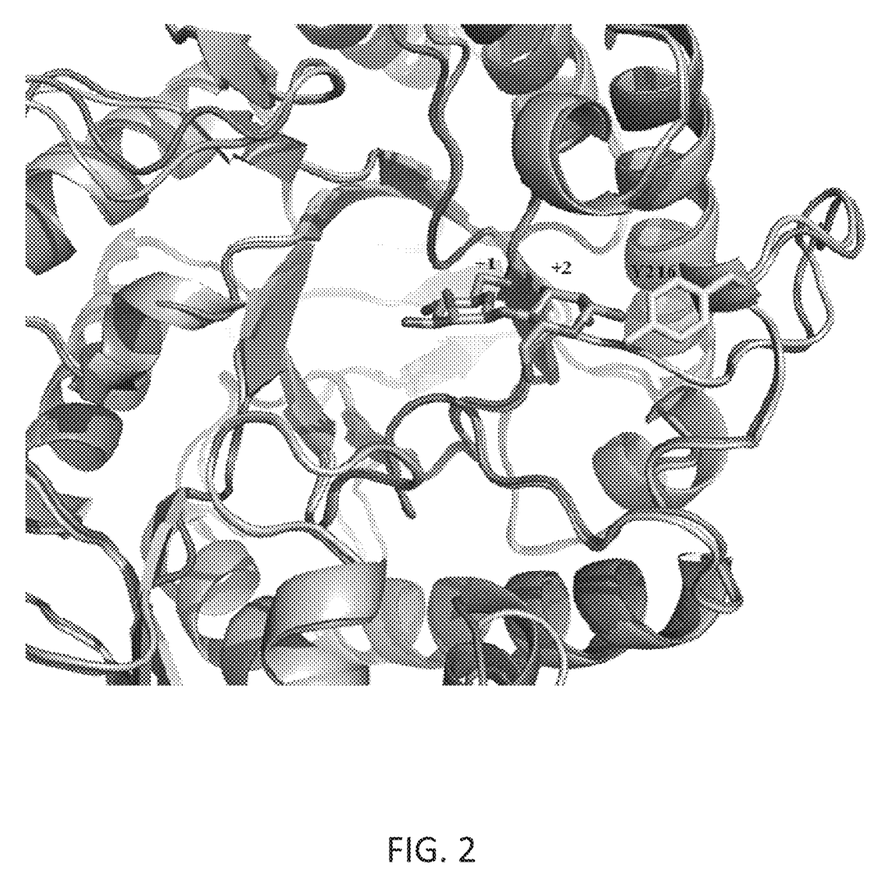
FIG. 2 shows the protein structure of the wild-type ManBK, which was superimposed with *Trichoderma reesei* mannanase in complex with mannobiose.

FIG. 2 shows the protein structure of ManBK solved by X-ray crystallography, and the solved structure was superimposed with *Trichoderma reesei* mannanase in complex with mannobiose in subsites +1 and +2. The protein structure of ManBK has $(β/α)_8$ barrel fold, wherein 8 β-sheets are located in the interior and 8 α-helixes pack around the exterior. By studying the structural information of ManBK, 30 amino acid residues were selected to be modified. Particularly, Tyr216 is located in the active site of the enzyme and may be important to the catalytic reaction of ManBK, and thus is targeted for site-directed mutagenesis, and it is found that the mutation of Tyr216 improves the enzymatic activity of ManBK, while other mutations do not show significant effects and are not redundantly described here. The following describes the processes for site-directed mutagenesis, protein expression and activity assay of Y216W mutant.

Figure 3:
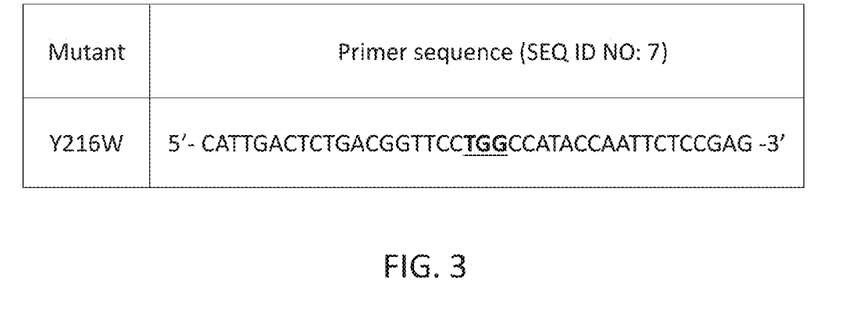
FIG. 3 shows the sequence of the mutagenic primer for the Y216W mutant.
Figure 4:
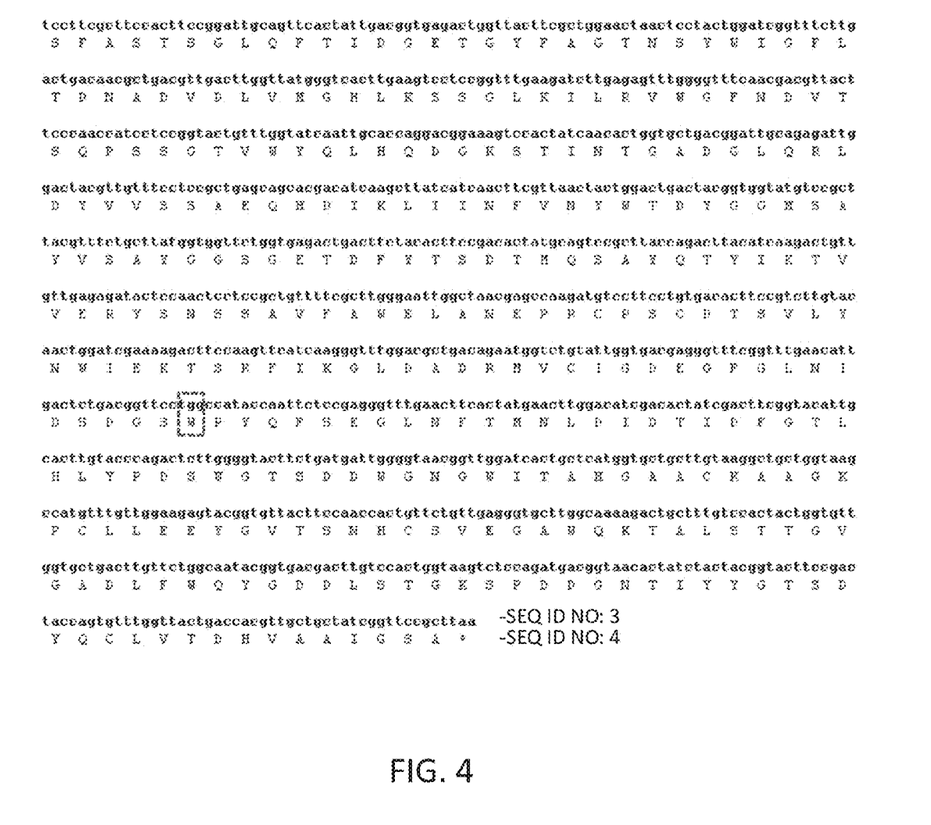
FIG. 4 shows the gene sequence and the amino acid sequence of the Y216W mutant.

The Y216W mutant was prepared by using QuikChange site-directed mutagenesis kit with ManBK gene as a template. The sequence (SEQ ID NO: 7) of the primer for Y216W mutant was shown in FIG. 3, wherein Y216W means Tyrosine at position 216 was mutated into Tryptophan; in other words, the modification is a substitution of Tyrosine at position 216 with Tryptophan. The original template was removed via DpnI digestion under 37° C., and then the plasmid with mutated gene was transformed into *E. coli* and screened with Ampicillin. Finally, the mutated gene was confirmed by DNA sequencing. Therefore, the Y216W mutant was constructed, and as shown in FIG. 4, the gene sequence was numbered as SEQ ID NO: 3, and the amino acid sequence was numbered as SEQ ID NO: 4.

The wild-type and mutant ManBK were expressed in *Pichia*. First, the plasmid DNA was linearized by PmeI and transformed into the *P. pastoris* X33 strain by electroporation. The transformants were selected on YPD (1% yeast extract, 2% peptone, 2% glucose, 2% agar) plates containing 100 μg/mL Zeocin and incubated at 30° C. for 2 days. The picked colonies were inoculated into 5 ml YPD medium at 30° C. overnight and further amplified into 50 ml BMGY medium at 30° C. overnight. After that, the cultured medium was changed to 20 ml BMMY with 0.5% methanol to induce the target protein expression. The samples were collected at different time points for every 24 hours, and meanwhile, the methanol was added into the flask to the final concentration of 0.5%. After induction for 4 days, the cells were harvested by centrifugation at 3500 rpm and the supernatant was collected for further purification.

The supernatant was purified by FPLC (fast protein liquid chromatography) using $Ni^{2+}$ column and DEAE column. Finally, the wild-type and mutant ManBK proteins, which had above 95% purity, were concentrated up to 5 mg/ml in protein buffer (25 mM Tris and 150 mM NaCl, pH 7.5) and then stored at −80° C.

To verify the difference between the wild-type and mutant ManBK, the β-mannanase activity assay and the kinetic analysis were performed. The β-mannanase activity was determined by dinitrosalicylic acid (DNS) method using mannose as a standard. The reaction was started by mixing 0.2 mL appropriately diluted enzyme sample with 1.8 mL of 3 mg/L locust bean gum (LBG) in 0.05 M citrate acid, pH 5.3. After 5-min incubation at 50° C., the reaction was stopped by adding 3 ml of DNS-reagent and boiled for 5 min to remove residual enzyme activity. After cooling in cold water bath for 5 min, the 540 nm absorbance of the reaction solution was measured. One unit of β-mannanase activity was defined as the amount of enzyme releasing 1 μmol of mannose equivalents per minute per mg of total soluble proteins under the assay conditions.

Figure 5:
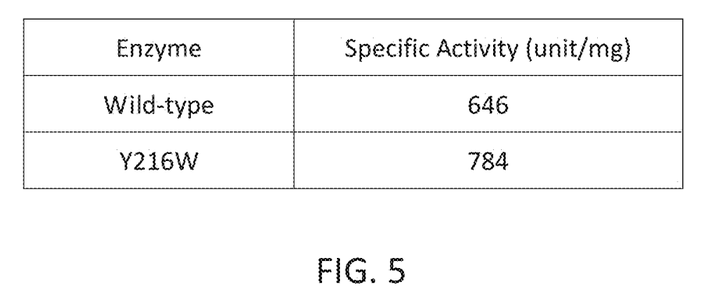
FIG. 5 shows the β-mannanase activity analysis of the wild-type ManBK and the Y216W mutant.

FIG. 5 shows the β-mannanase activity analysis of the wild-type ManBK and the Y216W mutant. The specific activity of the wild-type ManBK and the Y216W mutant are 646 and 784 U/mg. These results indicated that the specific activity of enzyme was increased 19% when Tyr216 was mutated to Tryptophan.

For the kinetic analysis, optimal protein concentration was first determined by using a series of 0.4-3.6 μg/ml protein solutions and 10 mg/ml LBG. The enzyme activity was then measured by using the optimal level of protein and a series of 0.5-10 mg/ml LBG solutions. Based on these data, the kinetic parameters were obtained by using the Michaelis-Menten model and curve-fitting analysis with a computer.

Figure 6:
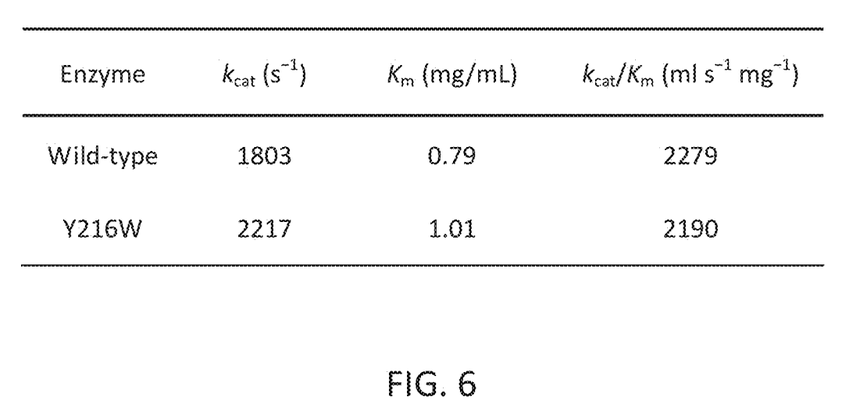
FIG. 6 shows the kinetic analysis of the wild-type ManBK and the Y216W mutant.

FIG. 6 shows the kinetic analysis of the wild-type ManBK and the Y216W mutant. The Y216W mutant had a higher catalytic rate ($k_{cat}$) than the wild-type enzyme while the $K_m$ value of the Y216W mutant was also slightly higher than that of the wild-type enzyme. Higher $K_m$ of an enzyme indicates lower affinity to the substrate. However, it also indicates faster substrate release rate. Therefore, with the presence of sufficient substrate in general industrial application, the specific activity of Y216W mutant was higher than that of the wild-type enzyme.

From the above, in order to improve the enzymatic activity of ManBK, the present invention solved the protein structure of the apo-form ManBK by X-ray crystallography, and the ManBK structure was superimposed with *Trichoderma reesei* mannanase complex structure. According to the superimposed structure, Tyr216 which is located in the active site is selected for site-directed mutagenesis and the tyrosine at position 216 was mutated into tryptophan to construct the Y216W mutant. From the β-mannanase activity assay and the kinetic analysis, the Y216W mutant exhibited significantly increased specific activity when compared to the wild-type, so it can reduce the production cost and will has more industrial applications. In addition, since ManBK has thermostability and can be applied to many industries with thermal processes, once the enzymatic activity thereof is increased, the production cost will be reduced and the profit will be increased. Therefore, the present invention successfully modified ManBK to improve the enzymatic activity thereof, and thus, the present invention possesses high industrial value.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A β-mannanase comprising a modified amino acid sequence of SEQ ID NO: 2, wherein the modification is a substitution of Tyrosine at position 216 with Tryptophan.

2. The β-mannanase according to claim 1 wherein the amino acid sequence of SEQ ID NO: 2 is encoded by ManBK gene isolated from *Aspergillus niger* BK01.

3. The β-mannanase according to claim 1 being an acidic and thermotolerant mannanase.

4. The β-mannanase according to claim 1 having a full length amino acid sequence of SEQ ID NO: 4.

5. The β-mannanase according to claim 1 wherein the β-mannanase is used in a food industry, a feed industry, or a paper pulp industry.

6. The β-mannanase according to claim 2 wherein the β-mannanase is used in a food industry, a feed industry, or a paper pulp industry.

7. The β-mannanase according to claim 3 wherein the β-mannanase is used in a food industry, a feed industry, or a paper pulp industry.

8. The β-mannanase according to claim 4 wherein the β-mannanase is used in a food industry, a feed industry, or a paper pulp industry.

* * * * *